(12) United States Patent
Taira et al.

(10) Patent No.: US 10,386,277 B2
(45) Date of Patent: Aug. 20, 2019

(54) CONTAINER FOR SPECIMEN PREPARATION

(71) Applicants: SEKISUI MEDICAL CO., LTD., Chuo-ku (JP); SEKISUI TECHNO MOLDING CO., LTD., Minato-ku (JP)

(72) Inventors: Hiroaki Taira, Chuo-ku (JP); Yuriko Nemoto, Chuo-ku (JP); Takuya Yotani, Chuo-ku (JP); Satoru Tominaga, Minato-ku (JP)

(73) Assignees: SEKISUI MEDICAL CO., LTD., Chuo-ku (JP); SEKISUI TECHNO MOLDING CO., LTD., Minato-ku (JP)

( * ) Notice: Subject to any disclaimer, the term of this patent is extended or adjusted under 35 U.S.C. 154(b) by 0 days.

(21) Appl. No.: 14/908,034

(22) PCT Filed: Jul. 25, 2014

(86) PCT No.: PCT/JP2014/069703
§ 371 (c)(1),
(2) Date: Jan. 27, 2016

(87) PCT Pub. No.: WO2015/012390
PCT Pub. Date: Jan. 29, 2015

(65) Prior Publication Data
US 2016/0169779 A1    Jun. 16, 2016

(30) Foreign Application Priority Data
Jul. 26, 2013   (JP) .................................. 2013-156176

(51) Int. Cl.
*G01N 1/38*   (2006.01)
*B01L 3/00*   (2006.01)
(Continued)

(52) U.S. Cl.
CPC ......... *G01N 1/38* (2013.01); *A61B 5/150022* (2013.01); *A61B 5/150343* (2013.01);
(Continued)

(58) Field of Classification Search
CPC ................ G01N 1/38; A61B 5/150022; A61B 5/150343
(Continued)

(56) References Cited

U.S. PATENT DOCUMENTS 4,024,857 A * 5/1977 Blecher ............ A61B 5/150022
                                                          422/419
4,396,024 A   8/1983 Sarstedt
(Continued)

FOREIGN PATENT DOCUMENTS

CN    102072949 A    5/2011
JP     49-2184 U1    1/1974
(Continued)

OTHER PUBLICATIONS

International Search Report dated Nov. 4, 2014, in PCT/JP2014/069703 Filed Jul. 25, 2014.
(Continued)

*Primary Examiner* — Jill A Warden
*Assistant Examiner* — Jacqueline Brazin
(74) *Attorney, Agent, or Firm* — Oblon, McClelland, Maier & Neustadt, L.L.P.

(57) ABSTRACT

A mechanism for collecting a trace of a biological sample to be used for a biological sample analysis, and for preparing a diluted solution of the sample. A container for specimen preparation includes: a biological sample collecting device; and a container for sample dilution. The biological sample collecting device includes: a capillary tube having openings formed at both ends thereof; and a support member for supporting the capillary tube. The container for sample
(Continued)

dilution includes: an opening; and a swirl flow generating member formed on an inner wall of the container for sample dilution. The capillary tube of the biological sample collecting device is arranged inside the container for sample dilution by the support member.

19 Claims, 8 Drawing Sheets

(51) Int. Cl.
- *A61B 5/15* (2006.01)
- *G01N 1/10* (2006.01)
- *B01F 11/00* (2006.01)
- *B01F 15/00* (2006.01)
- *G01N 35/00* (2006.01)

(52) U.S. Cl.
CPC .... *B01F 11/0074* (2013.01); *B01F 15/00876* (2013.01); *B01F 15/00883* (2013.01); *B01L 3/508* (2013.01); *B01L 3/5082* (2013.01); *B01L 3/50825* (2013.01); *G01N 1/10* (2013.01); *B01L 2200/025* (2013.01); *B01L 2200/026* (2013.01); *B01L 2300/041* (2013.01); *B01L 2300/044* (2013.01); *B01L 2300/046* (2013.01); *B01L 2300/047* (2013.01); *B01L 2300/06* (2013.01); *B01L 2300/0609* (2013.01); *B01L 2300/0838* (2013.01); *B01L 2300/0851* (2013.01); *B01L 2300/0858* (2013.01); *B01L 2400/086* (2013.01); *G01N 2001/383* (2013.01); *G01N 2035/00514* (2013.01)

(58) Field of Classification Search
USPC ........................................ 422/549
See application file for complete search history.

(56) References Cited

U.S. PATENT DOCUMENTS

| | | | | |
|---|---|---|---|---|
| 4,454,235 A | * | 6/1984 | Johnson | B01L 3/021 422/68.1 |
| 4,765,347 A | * | 8/1988 | Sensabaugh, Jr. | A24F 47/002 131/173 |
| 5,174,162 A | | 12/1992 | Miyake et al. | |
| 5,879,311 A | * | 3/1999 | Duchon | A61B 5/14532 600/573 |
| 5,882,594 A | | 3/1999 | Kawaguchi et al. | |
| 5,976,896 A | * | 11/1999 | Kumar | G01N 21/03 422/417 |
| 2003/0070498 A1 | * | 4/2003 | Ohyama | G01N 35/1079 73/863.01 |
| 2005/0074361 A1 | | 4/2005 | Tanoshima et al. | |
| 2005/0232813 A1 | | 10/2005 | Karmali | |
| 2006/0029520 A1 | | 2/2006 | Tanoshima et al. | |
| 2006/0115385 A1 | * | 6/2006 | Jon Meyer | A61B 10/0096 422/547 |
| 2008/0151683 A1 | * | 6/2008 | Meadows | B01F 13/0818 366/145 |
| 2008/0199900 A1 | * | 8/2008 | Signore | B01L 3/5021 435/29 |
| 2009/0311775 A1 | * | 12/2009 | Kocourek | B01F 11/0094 435/289.1 |
| 2012/0201724 A1 | | 8/2012 | Miyata et al. | |

FOREIGN PATENT DOCUMENTS

| | | | |
|---|---|---|---|
| JP | 49-2184 | * | 10/1974 |
| JP | 58-63037 | | 4/1983 |
| JP | 59-10839 U1 | | 1/1984 |
| JP | 59-65739 | | 5/1984 |
| JP | 61-191126 | | 11/1986 |
| JP | 03-41363 A | | 2/1991 |
| JP | H0341363 | * | 2/1991 |
| JP | 04-348250 A | | 12/1992 |
| JP | 08-304389 A | | 11/1996 |
| JP | 10-62432 A | | 3/1998 |
| JP | 2003-161675 A | | 6/2003 |
| JP | 2006-208167 | | 8/2006 |
| JP | 2012-137493 A | | 7/2012 |
| WO | WO 2009/090989 A1 | | 7/2009 |
| WO | WO 2009090989 | * | 7/2009 |

OTHER PUBLICATIONS

Extended European Search Report dated Jun. 12, 2017 in Patent Application No. 14830243.3.
Office Action dated Jun. 23, 2017, in Chinese Office Action No. 201480042008.2 (with machine translation).
Office Action dated Nov. 13, 2018, in Japanese Patent Application No. 2015-528355 (w/English translation), 4 pgs.

* cited by examiner

CONTAINER FOR SPECIMEN PREPARATION

FIELD OF THE INVENTION

The present invention relates to a container for specimen preparation, which is used for a biological sample analysis.

BACKGROUND OF THE INVENTION

Various types of automatic blood analyzer capable of analyzing a blood sample in a short period of time have been developed and put into practice. However, collected blood is not analyzed as it is, and is normally used for a variety of analyses after the blood is diluted. In addition, for analyses with high accuracy, it is necessary to sufficiently mix the blood and a diluting solution in order to precisely dilute the blood to a desired concentration. Therefore, it is desired that the automatic blood analyzer includes a means for mixing or stirring the blood and the diluting solution. For example, in Patent Literature 1, there is disclosed a liquid mixing container for diluting a blood sample. The liquid mixing container having a roughened inner wall, contains a liquid injection port formed in an upper part thereof for feeding a diluting solution, and an air injection port formed in a bottom thereof for injecting air for stirring liquid. Further, in Patent Literature 2, there is disclosed a system for diluting and mixing a specimen such as blood by discharging the specimen and a diluting solution into a container, and then repeatedly sucking and discharging the liquid in the container using a liquid dispensing means.

On the other hand, in recent years, there has been a need to conduct a blood test easily at a home, a bedside or the like. Therefore, there is required an analyzer capable of conducting a test in a non-invasive way using a smaller quantity of collected blood without collecting a large quantity of blood with the conventional blood collection tube. However, as a matter of course, as a quantity of a blood sample is smaller, a risk of losing the sample in a process of collecting the blood or in a process of adding and mixing the diluting solution becomes higher. Consequently, it is more difficult to precisely prepare a diluted solution of blood having a desired concentration.

CITATION LIST

Patent Literature

[PTL 1] JP-A-2003-161675
[PTL 2] JP-A-10-62432

SUMMARY OF THE INVENTION

Problem to be Solved by the Invention

It is an object of the present invention to provide a means for collecting a trace of a biological sample to be used for a biological sample analysis, and for preparing a diluted solution of the sample.

Means for Solving Problem

In order to achieve the above-mentioned object, the present invention provides a device for collecting a trace of a liquid biological sample, a container for sample dilution, which is capable of easily mixing the liquid biological sample and a diluting solution, and a container assembly for specimen preparation, which combines the device with the container for sample dilution.

That is, according to a first aspect of the present invention, there is provided a container for specimen preparation, comprising:
  a biological sample collecting device; and
  a container for sample dilution,
  the biological sample collecting device comprising:
    a capillary tube having openings formed at both ends thereof; and
    a support member for supporting the capillary tube,
  the container for sample dilution comprising:
    an opening; and
    a swirl flow generating member formed on an inner wall of the container for sample dilution, and
  the capillary tube of the biological sample collecting device being arranged inside the container for sample dilution by the support member.

Further, according to a second aspect of the present invention, there is provided a biological sample collecting device, comprising:
  a capillary tube having openings formed at both ends thereof; and
  a support member for supporting the capillary tube.

Further, according to a third aspect of the present invention, there is provided a container for sample dilution, comprising:
  an opening; and
  a swirl flow generating member formed on an inner wall of the container for sample dilution.

Effect of the Invention

According to the present invention, a trace of the biological sample can be collected. Further, according to the present invention, the trace of the sample can be diluted to a desired concentration with a simple means. Therefore, according to the present invention, the analysis result can be obtained with high accuracy even from the trace of the biological sample. The present invention is effective in conducting a simple test at a home or a bedside, or in preparing a specimen for a blood test to be conducted for a patient such as an infant, an elderly person, or a sickly person, who has difficulty in undergoing collection of blood by the conventional method or collection of a large quantity of blood.

BRIEF DESCRIPTION OF DRAWING

FIG. 1 is a view of an exemplary embodiment of a container for specimen preparation 1, in which FIG. 1(a) is a side view thereof, FIG. 1(b) is a sectional view thereof taken along the line A-A of FIG. 1(a), and FIG. 1(c) is a perspective view thereof.

FIG. 2 is a view of components of the container for specimen preparation 1 illustrated in FIG. 1, in which FIG. 2(a) is a front view of a biological sample collecting device 2, FIG. 2(b) is a front view of a container for sample dilution 3, FIG. 2(c) is a front view of a lid 4, and FIG. 2(d) is a view of the biological sample collecting device 2 fixed to the lid 4 arranged onto the container for sample dilution 3.

FIG. 4 is a view of an exemplary embodiment of the biological sample collecting device 2, in which FIG. 4(a) is a front view thereof, FIG. 4(b) is a sectional view thereof taken along the line A-A of FIG. 4(a), and FIG. 4(c) is a plan view thereof.

FIG. 5 is a view of the biological sample collecting device 2 fixed to the lid 4, in which FIG. 5(a) is a front view thereof, and FIG. 5(b) is a sectional view thereof taken along the line A-A of FIG. 5(a).

MODE FOR CARRYING OUT OF THE INVENTION

Figure 1:
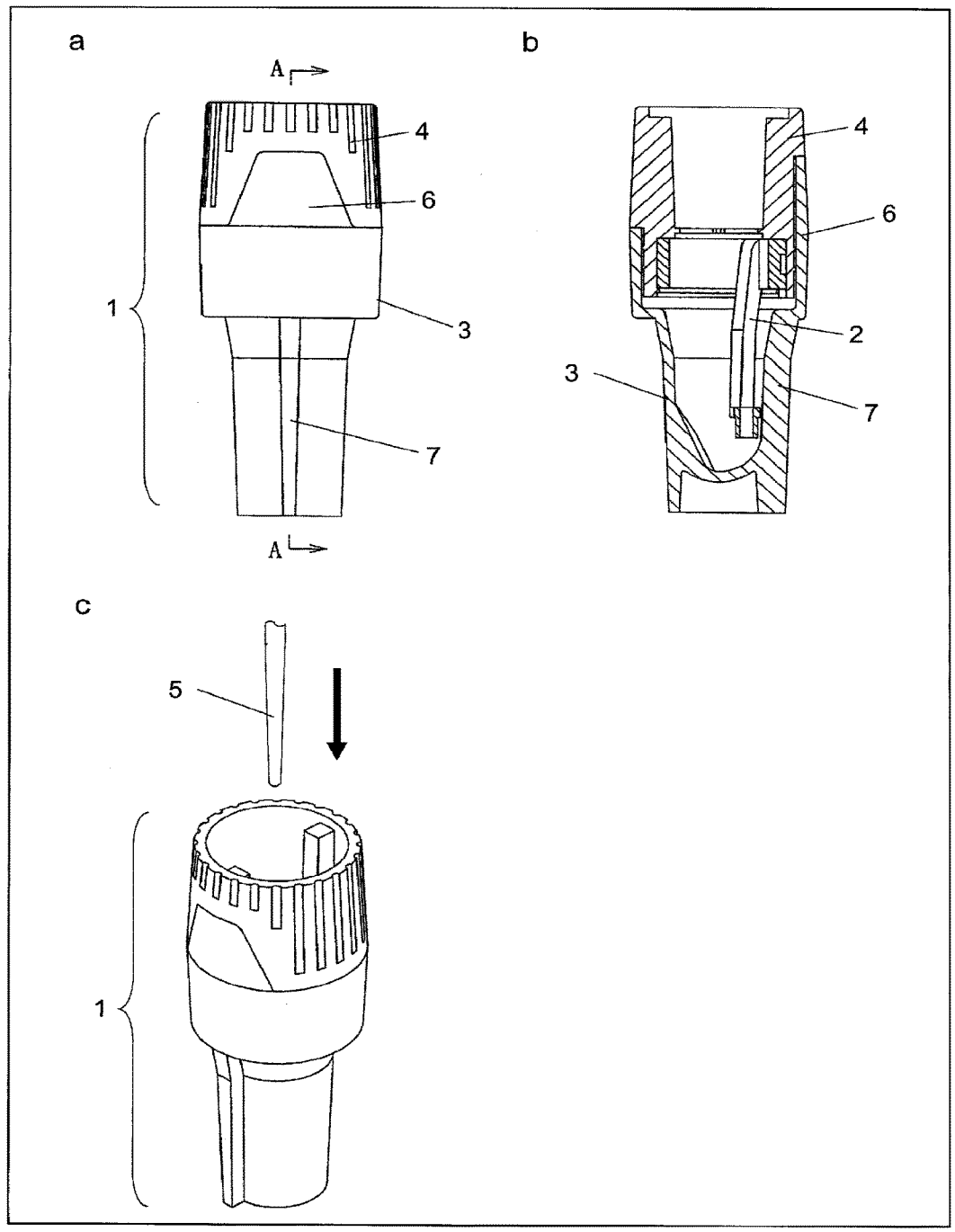

A container for specimen preparation according to the present invention is a device for preparing a specimen to be used for a biological sample analysis such as a blood test. As a biological sample to be prepared as a specimen in the container for specimen preparation according to the present invention, there is exemplified body fluid such as blood, serum, plasma, saliva, and urine, a solution or a suspension of feces or vomit, and a solution or a suspension of tissue and cells of animals and plants.

The container for specimen preparation according to the present invention comprises a biological sample collecting device for collecting a trace of the above-mentioned biological sample, and a container for sample dilution for diluting the collected biological sample with a diluting solution. The biological sample collecting device comprises a capillary tube for collecting and holding the biological sample. Further, the biological sample collecting device has a shape capable of being combined with the container for sample dilution, so that the capillary tube is arranged inside the container for sample dilution. The biological sample is collected and held by the capillary tube of the biological sample collecting device, and is arranged in the container for sample dilution when the device is set onto the container for sample dilution. Note that, the device and the container for sample dilution may be provided or used in combination, or may be provided or used separately.

The container for sample dilution comprises a swirl flow generating member formed on an inner wall thereof. The swirl flow generating member has a function of swirling liquid in the container for sample dilution when the liquid is injected into the container. Note that, the "swirl flow" used herein a means, for example, a flow swirling in a horizontal direction substantially along an inner peripheral surface of the container, a flow swirling in a vertical direction substantially along the inner peripheral surface of the container, and a flow swirling in a spiral manner substantially along the inner peripheral surface of the container. As an example, the swirl flow generating member is formed of a recess or a salient such as a slope, a protrusion, or a dent, which is formed on the inner wall of the container for sample dilution. When a sample diluting solution is injected into the container for sample dilution, the swirl flow of the diluting solution is generated inside the container owing to the swirl flow generating member formed on the inner wall of the container. The swirl flow causes the biological sample in the capillary tube arranged inside the container to flow out of the capillary tube, and to mix with the diluting solution sufficiently. As described above, using the container for specimen preparation according to the present invention, it is possible to easily prepare a homogeneous diluted solution of a trace of the biological sample.

The biological sample collecting device may be set onto the container for sample dilution manually or automatically, and the diluting solution may be injected into the container for sample dilution manually or automatically. When the biological sample collecting device is set onto the container for sample dilution automatically, the device may be transferred by a device transferring apparatus to be mounted onto the container for sample dilution. Alternatively, after transferring the device so that the capillary tube of the device is arranged inside the container for sample dilution, the device transferring apparatus may keep the device at the position as it is. When the biological sample collecting device is set onto the container for sample dilution automatically or the diluting solution is injected into the container for sample dilution automatically, it is preferred that a sign to be recognized by the device transferring apparatus or a diluting solution injecting apparatus be provided to the device, the container, or a rack in which the device and the container are accommodated.

A specimen prepared by the container for specimen preparation according to the present invention can be set in and analyzed by a general analyzer as it is. It is more preferred that the container for specimen preparation according to the present invention be set in the analyzer under a state in which the biological sample is received in the container, and that a series of processes, which encompasses from preparation of a diluted sample to analysis of a diluted sample, be performed in the analyzer automatically or semi-automatically. The specimen prepared by the container for specimen preparation according to the present invention is applicable to a variety of biological sample analyses using a high-speed liquid chromatography apparatus, a biochemical automatic analyzer, a hematocytometer, a flow cytometry, a flow injection apparatus, a grain size measuring apparatus, or the like.

Embodiment

An embodiment of the present invention is further described in detail with reference to the drawing. The embodiment of the present invention illustrated in the drawing is merely an example of the present invention, and the present invention is not limited thereto. It is needless to say that, in addition to the matter directly described in the embodiment, the present invention encompasses a variety of improvements and modifications made by a person skilled in the art within the scope of claims.

1. Container for Specimen Preparation

Figure 2:
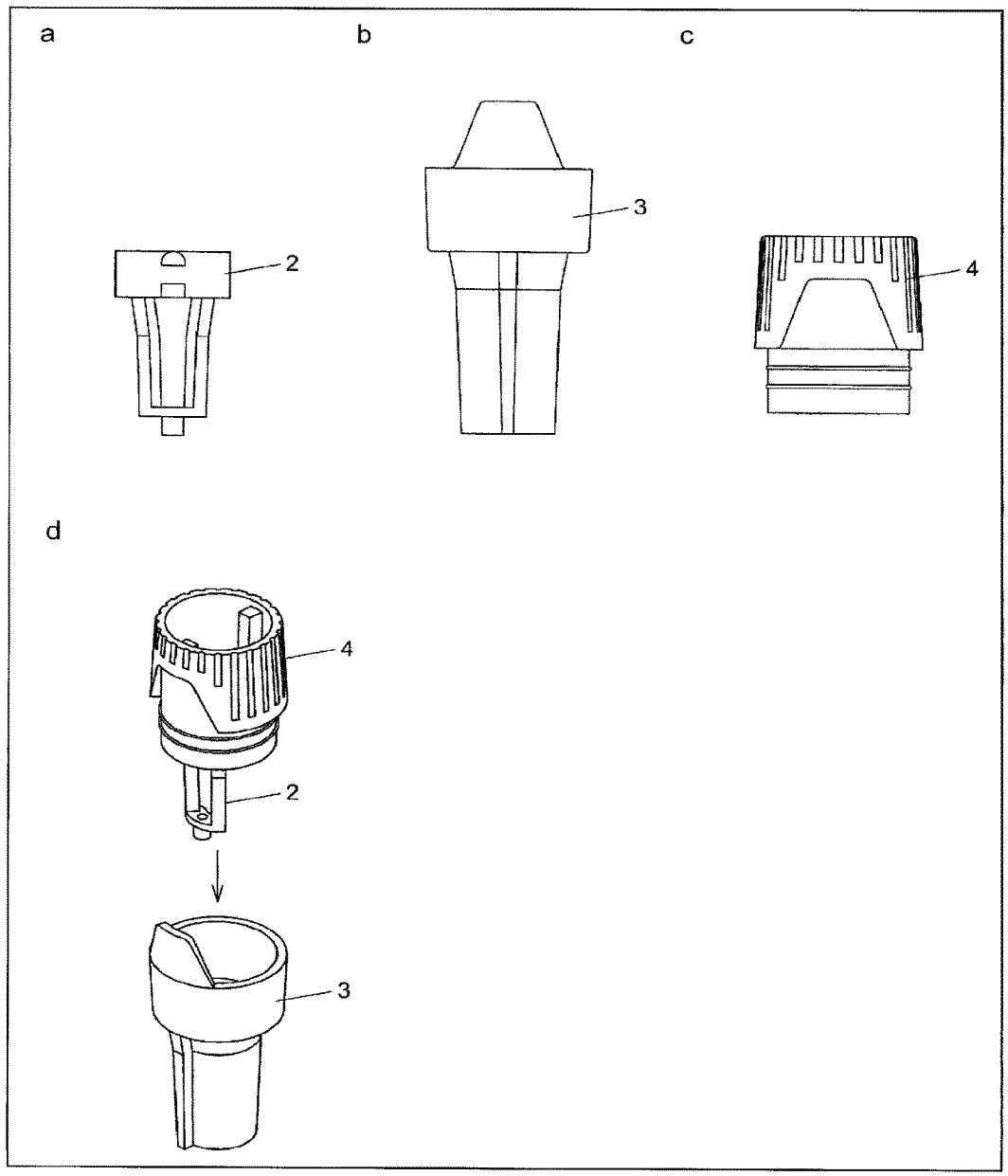

A container for specimen preparation 1 according to the present invention comprises a biological sample collecting device 2 and a container for sample dilution 3. The container for specimen preparation 1 may further comprise a lid 4 for closing an opening of the container for sample dilution 3. FIG. 1a, FIG. 1b, and FIG. 1c are a side view, a sectional view, and a perspective view of an exemplary embodiment of the container for specimen preparation 1 according to the present invention, respectively. The container for specimen preparation 1 illustrated in FIG. 1a comprises the biological sample collecting device 2, the container for sample dilution 3, and the lid 4. For reference, an injection tube 5 for injecting a sample diluting solution is further illustrated in FIG. 1c. The injection tube 5 passes through the lid 4 in a direction indicated by the arrow of FIG. 1c to be inserted into the container 3 through the opening of the container 3. In the container for specimen preparation 1 illustrated in FIG. 1, the biological sample collecting device 2, the container for sample dilution 3, and the lid 4 are manufactured as separate components as illustrated in FIG. 2a to FIG. 2c. However, when those components are combined together to construct the container for specimen preparation 1, as illustrated in FIG. 2d, the biological sample collecting device 2 is integrated with the lid 4, and the device 2 is arranged inside the container 3 under a state in which the container 3 is covered by the lid 4. Note that, the biological sample collecting device 2 and the container for sample dilution 3 may be used in combination as described above, and may be used separately.

2. Biological Sample Collecting Device

The biological sample collecting device 2 comprises a capillary tube 21 having openings formed at both ends of the capillary tube 21, for collecting a trace of the biological sample, and one or a plurality of support members 22 for supporting the capillary tube 21. The capillary tube 21 draws therein the biological sample due to a capillary phenomenon. For example, a fingertip or the like is caused to slightly bleed with a lancet or the like, and the capillary tube 21 is brought into contact with the bleeding portion. In this manner, a necessary quantity of blood is drawn into the capillary tube 21 due to the capillary phenomenon. Therefore, using the biological sample collecting device 2, a blood sample can be collected without involving invasion into a living body by a blood collection needle or the like. An inner diameter of the capillary tube 21 is large enough to cause the capillary phenomenon. The inner diameter is preferably from about 0.1 mm to about 3 mm, more preferably from about 0.5 mm to about 1.5 mm. A length of the capillary tube 21 is large enough to hold a necessary quantity of the biological sample for analysis, that is, large enough to hold preferably about 1 µL to about 5 µL of the biological sample, more preferably about 2 µL to about 4 µL of the biological sample.

Figure 3:
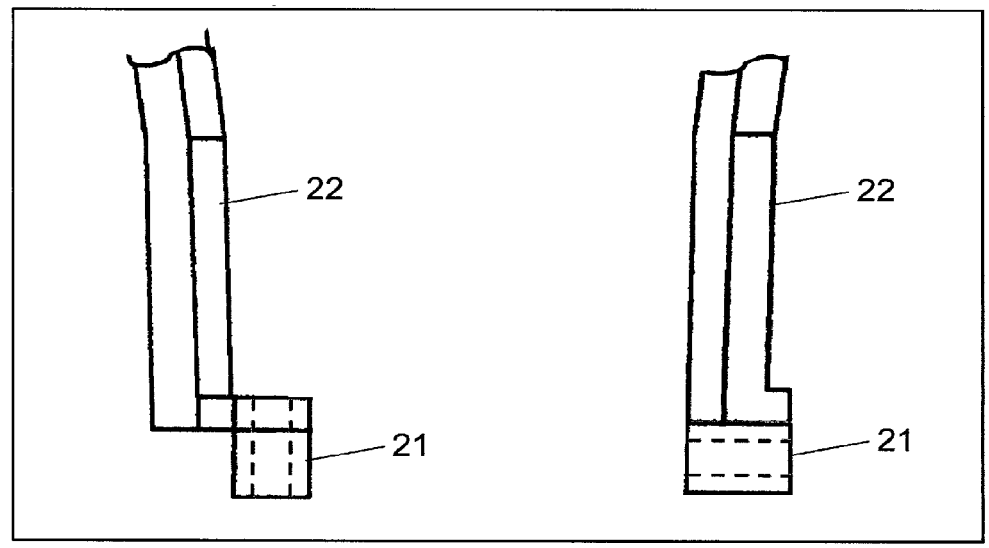
FIG. 3 is a partial side view of an exemplary embodiment of the biological sample collecting device 2 comprising a capillary tube 21 and support member 22.

The support member 22 supports the capillary tube 21, so that a position of the capillary tube 21 is maintained inside the container for sample dilution 3. The sample is held in the capillary tube 21 due to the capillary phenomenon. Thus, no limitation is imposed on a direction of the opening of the capillary tube 21 supported in the container 3, and the opening of the capillary tube 21 may be arranged to be open toward any directions including a horizontal direction and a vertical direction. FIG. 3 is a partial side view of an exemplary embodiment of the device 2, in which the opening of the capillary tube 21 supported in the container 3 is arranged to be open toward the vertical direction or the horizontal direction. On the other hand, in order to easily discharge the sample after injecting the diluting solution, it is preferred that the capillary tube 21 is arranged out of contact with an inner wall of the container 3.

Figure 4:
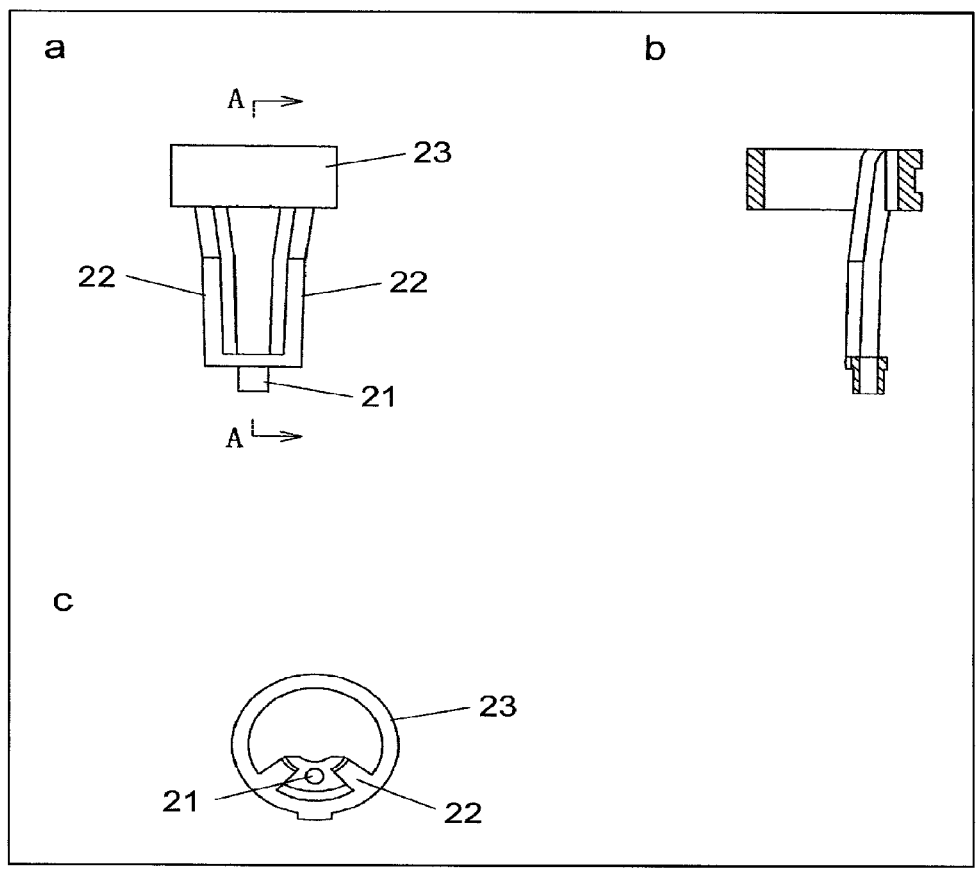
Figure 5:
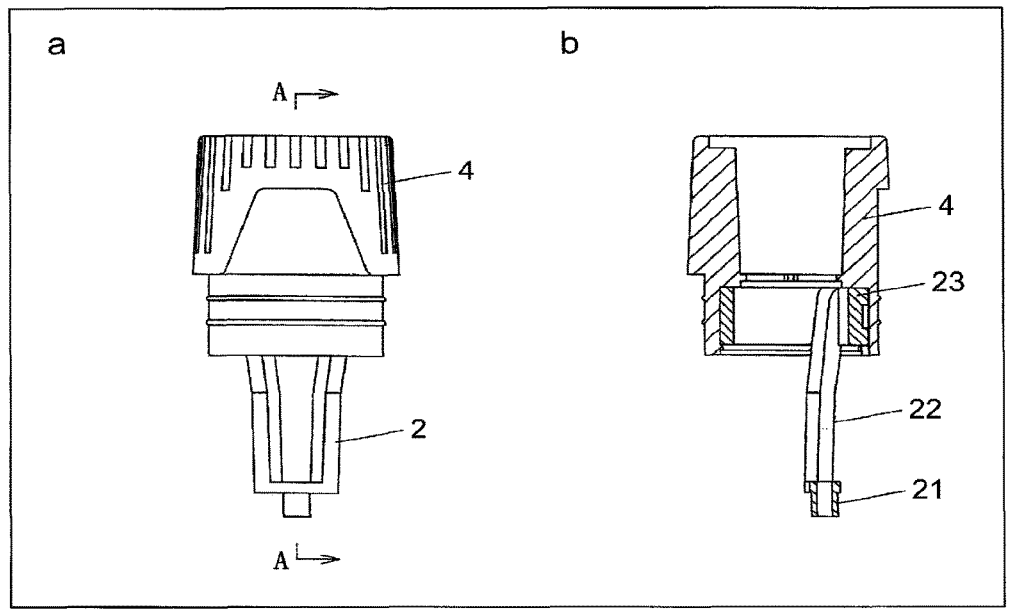
Figure 6:
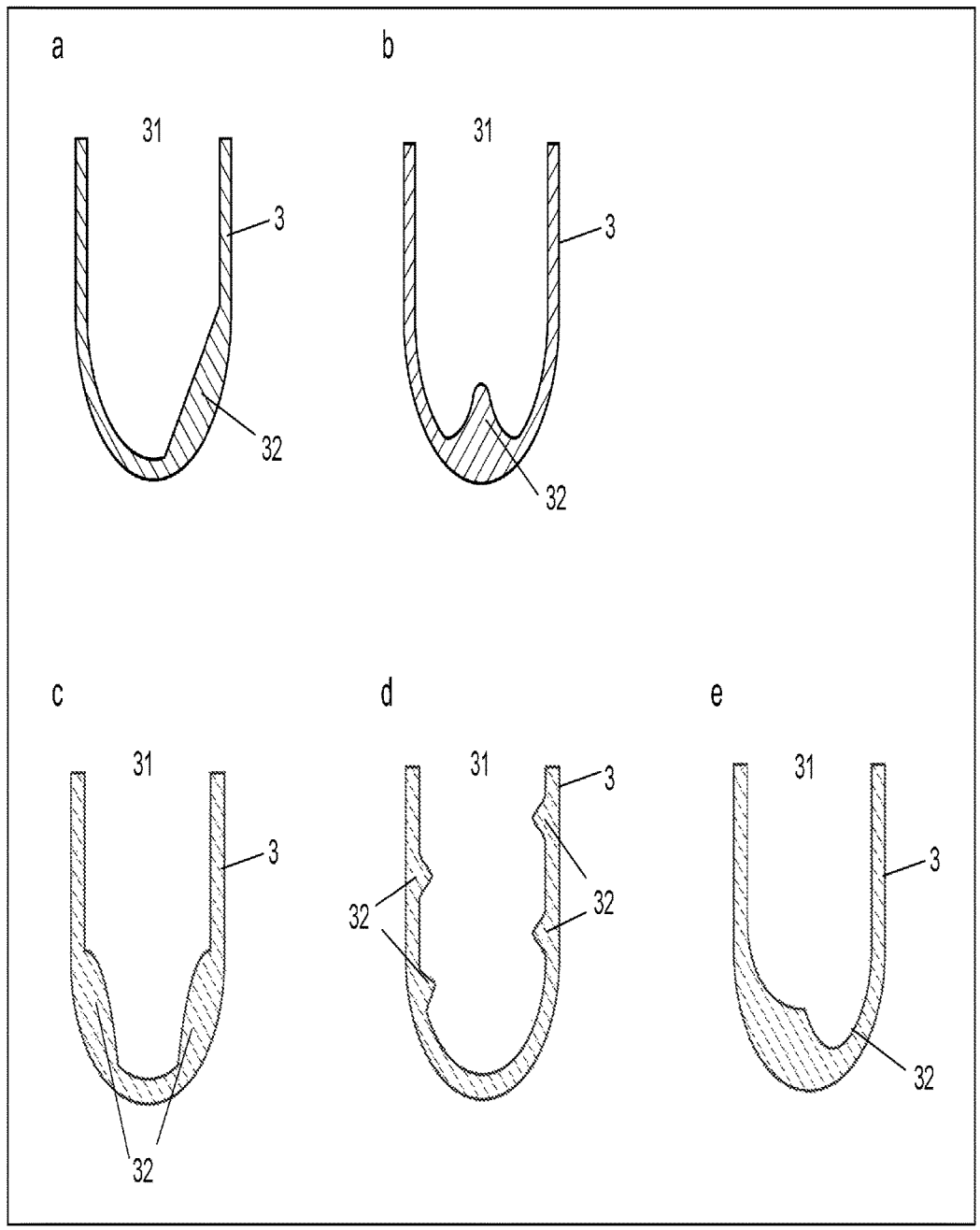
FIG. 6 is a sectional view of an exemplary embodiment of a swirl flow generating member 32 formed in the container for sample dilution 3.
Figure 7:
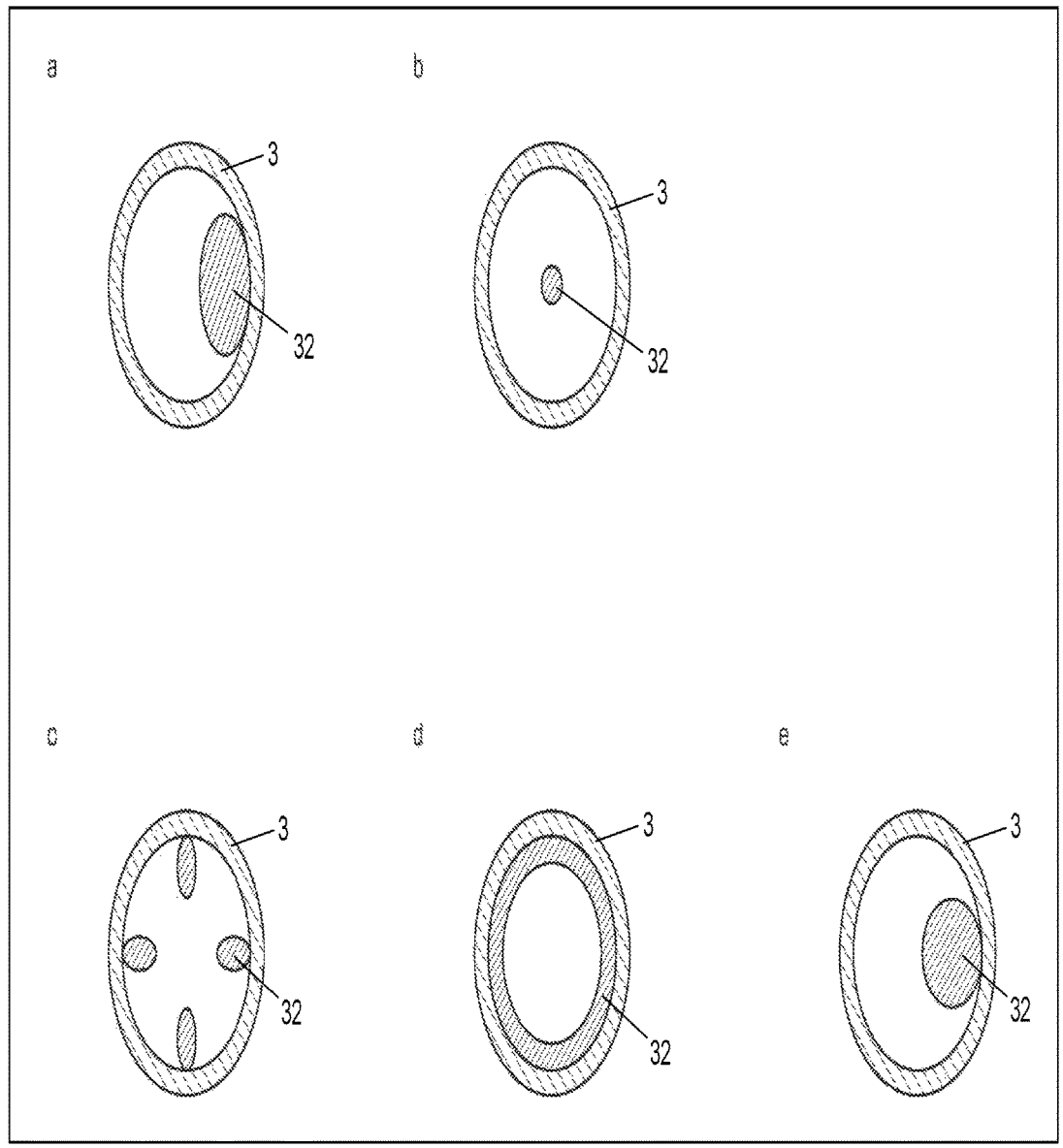
FIG. 7 is a plan view of the exemplary embodiment of the swirl flow generating member 32 formed in the container for sample dilution 3.
Figure 8:
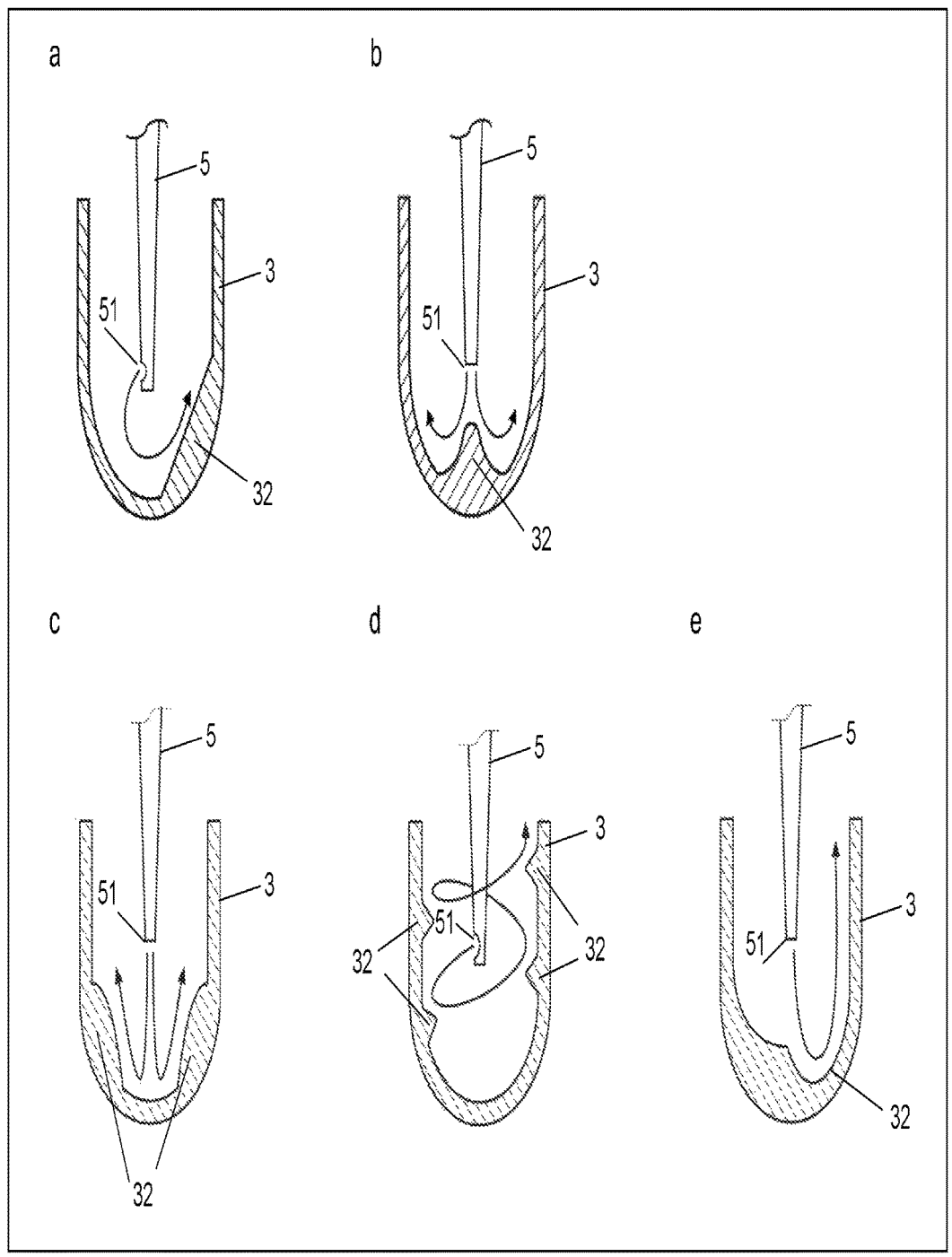
FIG. 8 is a conceptual view of swirl flows (indicated by the arrow) generated by a diluting solution discharged from an injection tube 5 into the container for sample dilution 3.

In the exemplary embodiment of the biological sample collecting device 2 illustrated in FIG. 4, the capillary tube 21 is supported by two support members 22. One end of each of the support members 22 is connected to the capillary tube 21, and the other end is connected to a fixing member 23 for fixing the device 2 to the lid 4. The fixing member 23 illustrated in FIG. 4 has an annular shape, and has structure capable of being fitted to an inner side of the tubular lid 4. FIG. 5 is an illustration of structure in which the biological sample collecting device 2 illustrated in FIG. 4 is fixed to the lid 4 by the fixing member 23. When the container 3 is covered by the lid 4 under the state in which the device 2 is fixed to the lid 4 as described above, the capillary tube 21 is inserted into and held in the container for sample dilution 3 owing to connection among the support members 22, the fixing member 23, and the lid 4 under a state in which the opening of the capillary tube 21 is open toward a specific direction (vertical direction in FIG. 5). Alternatively, the lid with the capillary tube as illustrated in FIG. 5 may be manufactured by previously forming the biological sample collecting device 2 and the lid 4 integrally with each other.

In another embodiment of the biological sample collecting device 2, the fixing member 23 has structure capable of being fixed directly to an edge of the opening of the container 3. When the device 2 is fixed to the container 3 by the fixing member 23, the capillary tube 21 is held inside the container 3 owing to connection between the support members 22 and the fixing member 23. Instill another embodiment, the biological sample collecting device 2 does not comprise the fixing member 23. Instead, one end of the support members 22 is connected to a device transferring apparatus. The device transferring apparatus is driven to transfer the capillary tube 21 to a desired position in the container 3, and then the capillary tube 21 is held therein.

The fixing member 23 have a structure capable of fixing the biological sample collecting device 2 to the container for sample dilution 3 or the lid 4. For example, the fixing member 23 may be formed into an annular shape, a U-shape, a hook shape or the like, but the shape of the fixing member 23 is not limited thereto.

As a material for the biological sample collecting device 2, for example, a polymethyl methacrylate resin, polystyrene, an ASA resin, a cycloolefin, polycarbonate, or polyethylene terephthalate or the like is preferred, and a polymethyl methacrylate resin or polystyrene is more preferred from the viewpoints of transparency and hydrophilicity. Further, it is preferred that the device 2 is formed by a molding method such as injection molding, hot press forming, cast molding, or three dimensional lamination molding. It is more preferred that the capillary tube 21, the support members 22, and the fixing member 23 are formed integrally with each other by injection molding.

3. Container for Sample Dilution

The container for sample dilution 3 has an opening 31. The above-mentioned capillary tube 21 and the above-mentioned injection tube 5 for injecting the diluting solution are inserted into the container 3 through the opening. A shape of a bottom of the container 3 is not particularly limited, and it is preferred that the container 3 is a cylindrical tube having a round bottom, a flat bottom, or a bottom having an intermediate shape between the round bottom and the flat bottom. The container 3 may further comprise a freestanding leg. A size of the container 3 may be appropriately changed, depending on a quantity of the diluting solution to be injected.

The diluting solution is injected into the container 3 from the injection tube 5. The injected diluting solution dilutes the biological sample held in the capillary tube 21. It is preferred that, in order to bring the diluting solution into contact with the biological sample so as to dilute the biological sample, the diluting solution is injected into the container 3 by such a quantity that the level of a surface of the injected diluting solution is at least higher than an upper end of the capillary tube 21. A swirl flow generating member 32 is formed on the inner wall of the container 3. When the diluting solution is injected, the solution comes into contact with the swirl flow generating member 32, thereby generating a swirl flow of the solution. The swirl flow has a function of causing the biological sample to flow out of the capillary tube 21, and a function of sufficiently mixing the biological sample flowing out of the capillary tube 21 with the diluting solution. Further, the solution in the container 3 is repeatedly sucked and discharged with the injection tube 5 or the like. In this manner, it is possible to stir the sample and the solution more efficiently.

Basically, the swirl flow generating member 32 is formed of one or a plurality of salients, or one or a plurality of recesss formed on a bottom of the inner wall of the container 3 or on a side wall of the container 3. Preferred examples of the one or the plurality of salients include one or a plurality of slopes, one or a plurality of ledge-like protrusions, one conical protrusion, one windmill-like, radial, or S-shaped protrusion, one, two, three, four, five, or more blade-form or spiral protrusions, and combination thereof. Preferred examples of the one or the plurality of recesss include one or a plurality of recesss formed in a part of the bottom. As the shape of the blade-form protrusion, there may be exemplified a straight shape, an arc shape, and a doglegged shape bending at an angle θ in a range of 90°≤θ≤180°. FIG. 6a to FIG. 6e are a sectional view of an exemplary embodiment of the swirl flow generating member 32 formed on the container for sample dilution 3, and FIG. 7a to FIG. 7e are a plan view thereof. In the example illustrated in FIG. 6a and FIG. 7a, the swirl flow generating member 32 is one slope formed to extend from a side surface of the inner wall of the container 3 toward the bottom thereof. In the example illustrated in FIG. 6b and FIG. 7b, the swirl flow generating member 32 is one conical protrusion formed at a center of the bottom of the container 3. In the example illustrated in FIG. 6c and FIG. 7c, the swirl flow generating member 32 is a plurality of blade-form protrusions formed on the bottom of the inner wall of the container 3. In the example illustrated in FIG. 6d and FIG. 7d, the swirl flow generating member 32 is one spiral protrusion formed to extend from the side surface of the container 3 toward the bottom thereof. In the example illustrated in FIG. 6e and FIG. 7e, the swirl flow generating member 32 is one recess formed at an off-center position to the bottom of the container 3. Thus, the container 3 has a two-step bottom. All of those shapes of the swirl flow generating member 32 represent an example thereof. As long as the swirl flow of the injected solution can be generated, the swirl flow generating member 32 may be attained by any number of recesss with any shape and any number of salient with any shape, such as a slope, a protrusion, and a dent, and by combination thereof. FIG. 8a to FIG. 8e are conceptual views of swirl flows of the solution (indicated by the arrow) generated inside the container 3 when the diluting solution is discharged from the injection tube 5 into the container 3 illustrated in FIG. 6a to FIG. 6e. Note that, in order to sufficiently attain an effect of the swirl flow, it is desired that the capillary tube 21 is arranged inside the container 3, so that a position of an upper end of the capillary tube 21 is level with or lower than a position of an upper end of the swirl flow generating member 32 formed on the inner wall of the container for sample dilution 3.

It is preferred that the container for sample dilution is formed of polypropylene, polyethylene, polystyrene, a polymethyl methacrylate resin, polyethylene terephthalate, polyamide, polybutylene terephthalate, polyacetal, or the like by injection molding or the like. It is more preferred that the swirl flow generating member 32 is formed integrally with the container 3.

4. Lid Portion

The lid 4 may be a cap, a screw cap, a lid, or the like for closing the opening of the container for sample dilution 3. In one embodiment, the lid 4 have a shape for sealing the opening of the container 3 when the lid 4 is put on the container 3 to which the biological sample collecting device 2 is fixed. In another embodiment, the lid 4 is connected to or formed integrally with the biological sample collecting device 2 (for example, see FIG. 5). When the container 3 is sealed by the lid 4, the biological sample collecting device 2 is fixed to the container 3 at the same time, and then the capillary tube 21 is held inside the container 3. In the case of the latter embodiment, the lid 4 can also function as the fixing member 23 of the device 2. Further, in the case of the latter embodiment, when the biological sample is collected using the biological sample collecting device 2, the lid 4 can also function as a handle for operating the device 2.

In order to enable the injection tube 5 to be inserted into the container for sample dilution 3, the lid 4 may further have a hole 42 formed in a wall 41 being a surface through which the injection tube passes. Alternatively, the lid 4 may comprise, instead of the wall 41 having the hole 42 formed therein, a film 43 capable of being pierced through by the injection tube. The hole 42 of the wall 41 have a size and a shape for enabling passage of the injection tube 5. Specifically, the hole 42 may be an orifice, or a straight, curved, cross-shaped, or radial slit. In order to prevent contamination of the sample in the container 3, it is preferred that the hole 42 is shaped into, for example, a straight, curved, cross-shaped, or radial slit that is usually closed and is openable only when the injection tube 5 passes through the slit. The slit may be open enough to prevent the solution in the container from splashing out of the container 3 due to surface tension of the solution. For example, when a sample to be diluted is blood, a width of the slit is preferably from 0.2 mm to 0.6 mm, more preferably from 0.3 mm to 0.5 mm. Depending on an outer diameter of the injection tube 5, when the width of the slit is smaller than 0.2 mm, the slit hinders passage of the injection tube 5. Further, when the width of the slit is larger than 0.6 mm, the sample solution may pass through the slit to leak out of the container.

Figure 9:
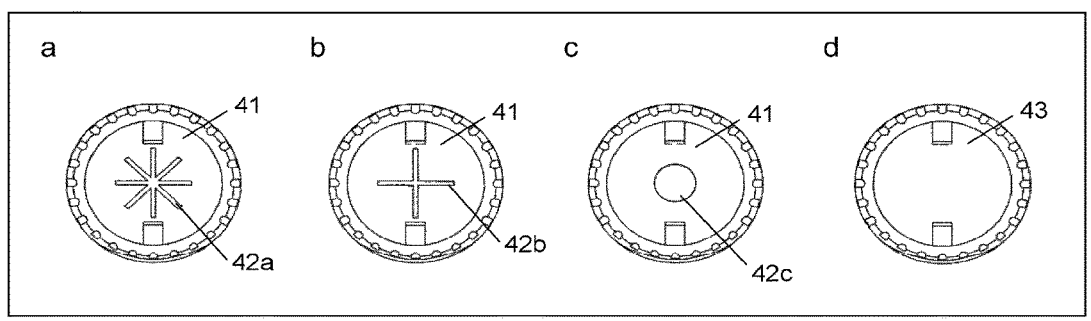
FIG. 9 is a view of the exemplary embodiment of a wall 41 of the lid 4.

In FIG. 9, an exemplary embodiment of the wall 41 of the lid 4 is illustrated. In FIG. 9a, the wall 41 has a radial slit 42a formed therein. In FIG. 9b, the wall 41 has a cross-shaped slit 42b formed therein. In those cases, when the injection tube 5 passes through the wall 41, a periphery of the slit on the wall 41 is pushed aside by the injection tube 5, thereby forming the hole 42. Accordingly, the injection tube 5 is easily inserted into the container 3. On the other hand, when the injection tube 5 is removed, the periphery of the slit is restored to its original shape. As a result, the hole 42 is closed, and the wall 41 is formed again, thereby being capable of sealing the container 3. In the example illustrated in FIG. 9c, the wall 41 always has an opening 42c through which the injection tube 5 passes. In the example illustrated in FIG. 9d, the wall 41 is the film 43 capable of being pierced through by the injection tube 5.

It is preferred that the lid 4 is formed of linear low-density polyethylene, polypropylene, high-density polyethylene, low-density polyethylene, polyamide, polyacetal, or the like. It is preferred that the wall 41 is formed of linear low-density polyethylene, polypropylene, high-density polyethylene, low-density polyethylene, polyamide, polyacetal, or the like. It is preferred that the film 43 is formed of linear low-density polyethylene, polypropylene, high-density polyethylene, low-density polyethylene, polyamide, polyacetal, or the like. Further, it is preferred that the film 43 is a thin layer capable of being easily pierced through by the injection tube. Further, it is preferred that the lid 4, the wall 41, and the film 43 are formed by injection molding or the like.

5. Injection Tube

The injection tube 5 has an outlet 51 formed therein, for discharging the diluting solution. It is preferred that the outlet 51 opens so as to be capable of discharging the diluting solution in such a direction that the swirl flow generating member 32 in the container for sample dilution 3 can generate the swirl flow. In one embodiment, the outlet opens to a side surface of the injection tube 5 at the vicinity of a distal end of the injection tube 5, and the diluting solution is discharged toward the side wall of the container for sample dilution 3 that faces the swirl flow generating member 32 of the container for sample dilution 3 (see FIG. 8*a*). In another embodiment, the outlet opens to a distal end of the injection tube 5, and the diluting solution is discharged toward the swirl flow generating member 32 formed on the bottom of the container for sample dilution 3 (see FIG. 8*b*). Note that, the injection tube 5 may be arranged in a manual injecting member, or may be arranged as a part of an automatic dispensing apparatus or an analyzer.

6. Guide

A guide 6 directs a connection position between the device 2 and the container 3 in order to keep the capillary tube 21 of the biological sample collecting device 2 at an appropriate position in the container for sample dilution 3. In one embodiment, the guide 6 comprises a pair of engaging members arranged in the device 2 and the container 3, respectively. With this configuration, the device 2 is fixed in a predetermined positional relationship with the container 3. Thus, the capillary tube 21 can be always arranged at a fixed position in the container 3. In another embodiment, the guide 6 comprises a pair of engaging members arranged in the container 3 and the lid 4 connected to the device 2. Instill another embodiment, the container 3 has an asymmetric shape such as a shape with a flat wall formed on a part of a circular opening. When the device 2 comprises a fixing member formed into an arc shape conforming to the shape of the circular opening, or the device 2 is connected to a cap formed into a shape conforming to the shape of the circular opening, the device 2 and the container 3 are always fixed to each other in the predetermined positional relationship. Thus, the capillary tube 21 can be arranged at the fixed position in the container 3. Note that, in still another embodiment, the guide 6 may be a mark such as a line, a groove, and a protrusion, which is put on the device 2 and the container 3, respectively. In FIG. 1 described above, the guide 6 comprises a pair of engaging members arranged in the lid 4 and the container 3, respectively. The lid 4 connected to the device 2 is mounted onto the container 3, thereby keeping the capillary tube 21 of the device 2 at a predetermined position in the container 3.

7. Engaging Member

When the container for specimen preparation 1 according to the present invention is aligned on a rack, an engaging member 7 functions to arrange the container 1 in a predetermined direction with respect to the rack. Further, when the rack having the container 1 aligned thereon is set onto a dispensing apparatus or an analyzer, arrangement of the container 1 in the apparatus is fixed. Thus, container 1 can be arranged in the apparatus at a position suitable for dispensing or analysis. The engaging member 7 is formed into a shape capable of stably fixing and arranging the container 1 on the rack. Thus, the engaging member 7 can be formed at any position in the container for sample dilution 3 or in the lid 4. It is preferred that the engaging member 7 is an engaging member such as a protrusion or a hook formed on the container for sample dilution 3, and that the engaging member 7 be engaged with a counterpart member formed on the rack, thereby fixing the container 1 on the rack. In FIG. 1 described above, the engaging member 7 is an elongated protrusion formed on an outer wall of the container for sample dilution 3 along a longitudinal direction thereof. Note that, the engaging member 7 may be formed integrally with the container for sample dilution 3, or may be formed as a separate member and connected to the container for sample dilution 3. It is preferred that the engaging member 7 is formed integrally with the container for sample dilution 3.

REFERENCE SIGNS LIST

1 container for specimen preparation
2 biological sample collecting device
3 container for sample dilution
4 lid
5 injection tube
6 guide
7 engaging member
21 capillary tube
22 support member
23 fixing member
31 opening
32 swirl flow generating member
41 wall
42*a* radial slit
42*b* cross-shaped slit
42*c* opening
43 film
51 outlet

The invention claimed is:

1. A container for specimen preparation, comprising:
a biological sample collecting device; and
a container for sample dilution,
the biological sample collecting device comprising:
a capillary tube having openings formed at both ends thereof; and
a support member for supporting the capillary tube,
the container for sample dilution comprising:
an opening;
a swirl flow generating member formed integrally in an inner wall of the container for sample dilution where the inner wall has differing thicknesses; and
an outer wall of the container where the outer wall is curved and independent of the shape of the swirl flow generating member,
the capillary tube of the biological sample collecting device being arranged inside the container for sample dilution by the support member so that a position of an upper end of the capillary tube is level with or lower than a position of an upper end of the swirl flow generating member,
the capillary tube of the biological sample collecting device being arranged inside the container for sample dilution by the support member so that a position of the capillary tube is offset from a central axis of the container for sample dilution.

2. The container for specimen preparation according to claim 1, wherein the biological sample collecting device further comprises a fixing member for fixing the biological sample collecting device to the container for sample dilution, so that the capillary tube of the biological sample collecting device is arranged in the container for sample dilution.

3. The container for specimen preparation according to claim 1, further comprising a lid for closing the opening of the container for sample dilution.

4. The container for specimen preparation according to claim 3, wherein a fixing member comprises the lid.

5. The container for specimen preparation according to claim 3, wherein the lid has a hole formed therein to allow passage of an injection tube for injecting a liquid into the container for sample dilution, or the lid comprises a film capable of being pierced through by the injection tube.

6. The container for specimen preparation according to claim 1, further comprising a guide for arranging the capillary tube of the biological sample collecting device at a desired position in the container for sample dilution.

7. The container for specimen preparation according to claim 1, further comprising an engaging member for retaining the container for specimen preparation in a predetermined direction on a rack.

8. A biological sample collecting device, comprising:
a capillary tube having openings formed at both ends thereof; and
a support member for supporting the capillary tube,
wherein the capillary tube of the biological sample collecting device is arranged inside a container by the support member so that a position of an upper end of the capillary tube is level with or lower than a position of an upper end of a swirl flow generating member, the container comprising an opening and the swirl flow generating member formed integrally in an inner wall of the container where the inner wall has differing thicknesses and an outer wall of the container where the outer wall is curved and independent of the shape of the swirl flow generating member, and
wherein the capillary tube of the biological sample collecting device is arranged inside the container by the support member so that a position of the capillary tube is offset from a central axis of the container.

9. A container for sample dilution, comprising:
an opening;
a swirl flow generating member formed integrally in an inner wall of the container for sample dilution where the inner wall has differing thicknesses; and
an outer wall of the container where the outer wall is curved and independent of the shape of the swirl flow generating member,
wherein a capillary tube of a biological sample collecting device is arranged inside the container for sample dilution by a support member so that a position of an upper end of the capillary tube is level with or lower than a position of an upper end of the swirl flow generating member, the biological sample collecting device comprising the capillary tube having openings formed at both ends thereof, and the support member for supporting the capillary tube,
the capillary tube of the biological sample collecting device being arranged inside the container for sample dilution by the support member so that a position of the capillary tube is offset from a central axis of the container for sample dilution.

10. The container for specimen preparation according to claim 1, wherein the swirl flow generating member comprises at least one of:
a slope formed to extend from a side surface of the inner wall of the container for sample dilution toward a bottom of the inner wall of the container for sample dilution;
a conical protrusion formed on the side surface of the inner wall of the container for sample dilution or on a center of the bottom of the inner wall of the container for sample dilution;
a plurality of blade-form protrusions formed on the bottom of the inner wall of the container for sample dilution;
a spiral protrusion formed to extend from the side surface of the inner wall of the container for sample dilution toward the bottom of the inner wall of the container for sample dilution; and
a recess formed at an off-center position to the bottom of the container for sample dilution.

11. The container for sample dilution according to claim 9, wherein the swirl flow generating member comprises at least one of:
a slope formed to extend from a side surface of the inner wall of the container for sample dilution toward a bottom of the inner wall of the container for sample dilution;
a conical protrusion formed on the side surface of the inner wall of the container for sample dilution or on a center of the bottom of the inner wall of the container for sample dilution;
a plurality of blade-form protrusions formed on the bottom of the inner wall of the container for sample dilution;
a spiral protrusion formed to extend from the side surface of the inner wall of the container for sample dilution toward the bottom of the inner wall of the container for sample dilution; and
a recess formed at an off-center position to the bottom of the container for sample dilution.

12. The container for specimen preparation according to claim 1, wherein the capillary tube is disposed at a distal aspect of the support member for supporting the capillary tube so that a dimension of the capillary tube is perpendicular to the distal aspect of the support member.

13. The container for specimen preparation according to claim 1, wherein the capillary tube is disposed at a distal aspect of the support member for supporting the capillary tube so that a dimension of the capillary tube is parallel to the distal aspect of the support member.

14. The container for specimen preparation according to claim 1, wherein the capillary tube of the biological sample collecting device is arranged inside the container for sample dilution by the support member so that the capillary tube is lower than an upper end of the swirl flow generating member.

15. The container for specimen preparation according to claim 1, wherein the swirl flow generating member is formed integrally in an inner wall of a distal portion of the container for sample dilution where the inner wall has differing thicknesses.

16. The container for specimen preparation according to claim 1, wherein the swirl flow generating member is formed integrally on a bottom, a side, or a combination thereof, of an inner wall of the container for sample dilution where the inner wall has differing thicknesses.

17. The container for specimen preparation according to claim 1,
wherein the capillary tube of the biological sample collecting device is arranged inside the container for sample dilution by the support member so that the openings formed at both ends of the capillary tube are level with or lower than a position of an upper end of the swirl flow generating member such that a level of a surface of an injected diluting solution is at least higher than the upper end of the capillary tube.

18. The biological sample collecting device according to claim 8,
wherein the capillary tube of the biological sample collecting device is further arranged inside the container by the support member so that the openings formed at both ends of the capillary tube are level with or lower than the position of the upper end of the swirl flow generating member such that a level of a surface of an injected diluting solution is at least higher than the upper end of the capillary tube.

19. The container for sample dilution according to claim 9,
wherein the capillary tube of the biological sample collecting device is arranged inside the container by the support member so that openings formed at both ends of the capillary tube are level with or lower than a position of an upper end of the swirl flow generating member such that a level of a surface of an injected diluting solution is at least higher than the upper end of the capillary tube.

* * * * *